United States Patent [19]

Smit

[11] Patent Number: 4,643,723

[45] Date of Patent: Feb. 17, 1987

[54] DEVICE FOR ADMINISTERING A LIQUID IN A NUMBER OF DOSES

[76] Inventor: Cornelis Smit, Heussenstraat 70, 2023 JG Haarlem, Netherlands

[21] Appl. No.: 811,804

[22] Filed: Dec. 19, 1985

[30] Foreign Application Priority Data

Dec. 24, 1984 [NL] Netherlands .......................... 8403937

[51] Int. Cl.⁴ ............................................. A61M 5/00
[52] U.S. Cl. .................................... 604/207; 604/236; 604/256
[58] Field of Search ............... 604/207, 208, 236, 237, 604/187, 213, 215, 221, 222, 246, 255, 257, 247

[56] References Cited

U.S. PATENT DOCUMENTS 3,957,052  5/1976  Topham .............................. 604/236
4,449,693  5/1984  Gereg ............................... 604/236 X

*Primary Examiner*—John D. Yasko
*Attorney, Agent, or Firm*—Blum, Kaplan, Friedman, Silberman & Beran

[57] ABSTRACT

A device for administering a liquid in a number of doses, such as insulin to a patient, comprising a piston (3) in a pump chamber (4), a cannula (5) being connectable to the pump chamber, a piston rod (14) connected to the piston and having an operating button (25), a valve (1) and a reservoir (2), wherein by retracting the piston (3), at the same time the reservoir is connected to the pump chamber (4) through the valve in order to fill the pump chamber and the valve is moved into the position for closing the connecting element (6) between the pump chamber and the cannula (5) and wherein, by moving the piston forward, at the same time the connecting element between the pump chamber and the cannula is connected through the valve to the pump chamber and the valve is moved into the position for closing the passage (7) between the reservoir and the pump chamber.

17 Claims, 6 Drawing Figures

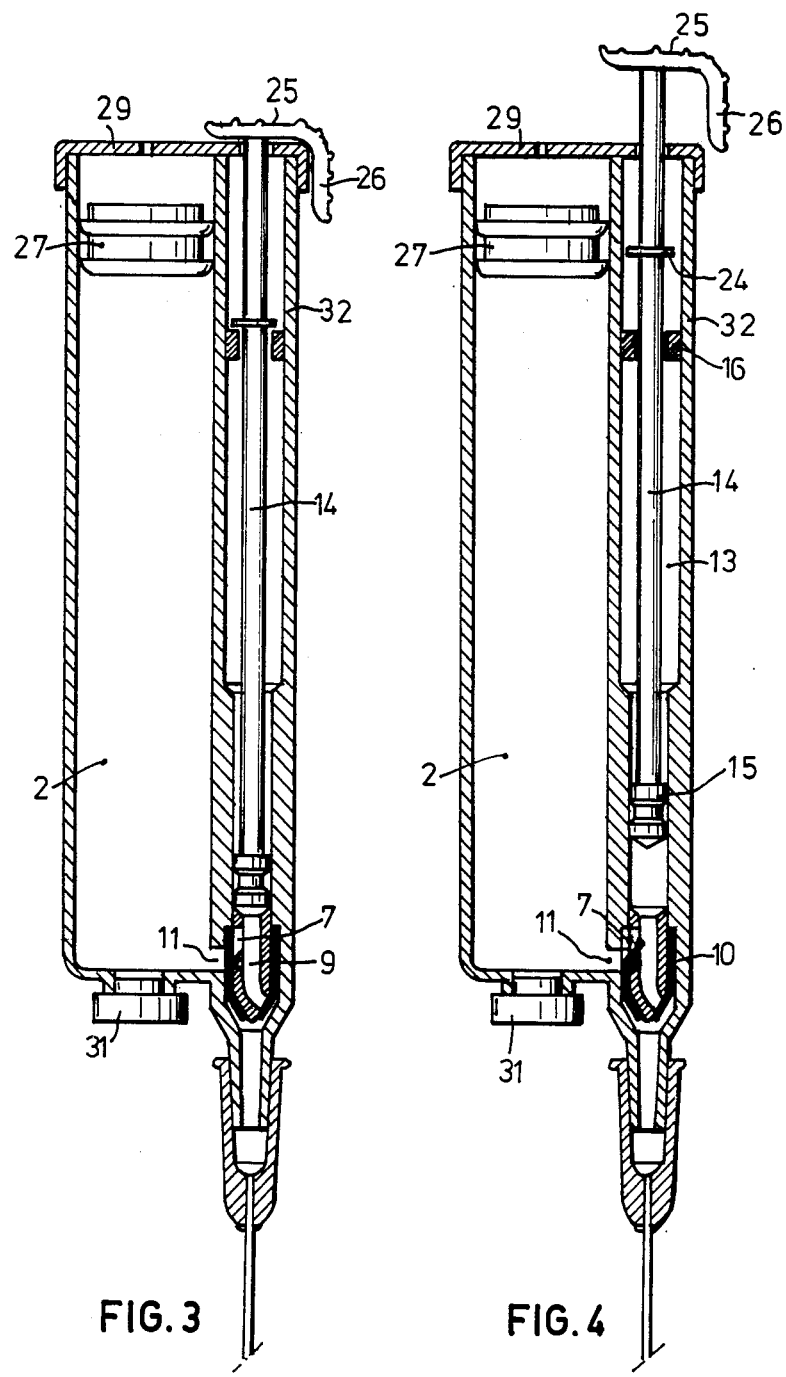

DEVICE FOR ADMINISTERING A LIQUID IN A NUMBER OF DOSES

The invention relates to a device for administering a liquid in a number of doses, such as insulin to a patient, said device comprising a piston being reciprocatably disposed in a pump chamber, a cannula being connectable to the pump chamber and a piston rod connected to the piston and having an operating button.

The invention aims in particular at a device with which the quantity of liquid per dose can be accurately measured out and in which the liquid comes from a prefilled reservoir. With the invented device, for example a diabetes patient can administer insulin to himself several times in the course of the day and during for example ten days, after which the device is empty and can be disposed of. However, the invented device is by no means restricted to administering insulin, but can also be applied for administering other liquids, such as an antibiotic, or for a painkiller to a carcinoma patient or for liquids which have to be administered parenterally. The invented device can also be used for subcutaneous, intravenous and/or intramuscular administering of liquid and it can be applied in an infusion set.

For instance for ambulant diabetes patients it is now necessary to keep a supply of insulin at home so that a patient can administer an accurately measured out quantity of insulin, for example 0.2 cc, to himself, a few times a day, e.g. 2 or 3 times a day, with the aid of a normal hypodermic syringe. In order to do so, the patient, who is a layman in the field of medicine, has to perform a series of actions in which mistakes can be made. Those mistakes could lead to adverse effects on the patient, due to for instance air bubbles entering the patient with the liquid, or an incorrect dose or unhygenic circumstances. The object of the present invention is to reduce the number of actions to be performed by the patient so as to reduce the chance of mistakes. This is attained because the invented device is easier to operate and incorporates less possibilities of making operational errors, which is important for instance to people having a visual handicap, motory disturbances, stiffness in the joints or failing mental abilities, i.e. complaints which occur especially in older people, whereas especially older people often have no relatives who can offer help, so that they need help from professional nursing staff, which is very expensive for a patient staying at home. However, careless operation easily occurs, also with children.

According to the invention, these drawbacks are removed since the invented device has been provided with a valve and a reservoir, in which by retracting the piston, at the same time the reservoir is connected to the pump chamber through the valve in order to fill the pump chamber and the valve is moved into the position for closing the connecting element between the pump chamber and the cannula and wherein, by moving the piston forward, at the same time the connecting element between the pump chamber and the cannula is connected through the valve to pump chamber and the valve is moved into the position for closing the passage between the reservoir and the pump chamber.

This reduces the number of actions to be performed, which reduces the chance of mistakes. For it is for instance not necessary to accurately measure out the dose, since the content of the pump chamber is equal to the dose to be administered. It is also impossible for air bubbles to enter the patient because the reservoir and the pump chamber form a closed system which cannot be broken by the patient, in which the liquid from the reservoir is sucked directly into the pump chamber, which is contrary to a normal hypodermic syringe, the needle of which has to be put in a capsule containing liquid by the patient so as to suck the liquid into the pump chamber, during which too little or too much liquid can be sucked up, or air can be also sucked up if the needle has not been put deep enough into the liquid.

Preferably the invented device is provided with a cheap and therefore disposable double check valve which according to the invention consists of a sleeve about a body, a channel extending trough the body, between the pump chamber and the connecting element for the cannula and a passage in the body branching off from the channel and communicating with the reservoir and in that the sleeve is of elastic material and in unburdened condition closes off both the outlet of the channel to the cannula and the outlet of the reservoir to the passage, whereas the sleeve portion at the outlet of the channel can only be pushed aside elastically by piston pressure exerted in the pump chamber and the upper rim of the sleeve reaches exactly up to the upper side of the passage to the reservoir, so that under subatmospheric pressure created by retracting the piston in the pump chamber, the sleeve contracts elastically so that the passage is open, whereas the sleeve near the passage completely covers the outlet of the reservoir during superatmospheric pressure in the passage.

According to the invention, the largest diameter of the connecting element between the valve and the cannula can be small since the end of the valve body facing away from the pump chamber is cone-shaped, wherein the outlet of the channel debouches at the cone surface and inclines with respect to the central axis of the valve body.

In order to enable the doses to be measured out accurately, it is necessary to completely fill the pump chamber every time with liquid, which is accomplished by completely retracting the piston every time. According to the invention, this complete retraction of the piston is automatically attained by a subatmospheric pressure chamber wich is situated in alignment with the pump chamber and in which a pressure lower than atmospheric pressure prevails, wherein the subatmospheric pressure chamber is sealed airtight with respect to the pump chamber by a partition which is fixedly mounted on the piston rod and which seals slidably against the wall portion above the pump chamber and wherein the other end of the subatmospheric pressure chamber is sealed air-tight by a stationary partition through which the piston rod extends slidably and in a sealing manner.

According to the invention, automatically retracting the piston in order to completely fill the pump chamber can also be attained by a superatmospheric pressure chamber which is situated in alignment with the pump chamber and in which a pressure higher than atmospheric pressure prevails, wherein the superatmospheric pressure chamber is sealed airtight with respect to the pump chamber by a stationary partition through which the piston rod extends slidably and in a sealing manner and wherein the other end of the superatmospheric pressure chamber is sealed airtight by a partition which is mounted fixedly on the piston rod and which slidably seals against the wall of the superatmospheric pressure chamber.

A third embodiment of the invented device having means for automatically retracting the piston in order to completely fill the the pump chamber, is characterized by a spring chamber which is situated in alignment with the pump chamber and which contains a spring bearing on a support secured near the pump chamber and biasing against a cam secured on the piston rod.

The pump chamber of the invented device is able to contain a standard quantity of liquid to be injected, for example 0.2 cc insulin, but often it is necessary to inject a smaller dose, for example with children. Injecting an accurate smaller dose is, according to the invention, possible because the operating button is provided with at least one appendix extending downwardly along the piston rod to such an extend as corresponds with the desired limited quantity of liquid to be administered from the pump chamber, wherein this appendix encounters the upper wall of the device when pushing the piston, and wherein the piston, the piston rod and the operating button are rotatable about their central axes in order to rotate the appendix into a position alongside the upper wall of the device in order to be able to empty the pump chamber completely.

The invented device is compact because the reservoir extends along the pump chamber plus the subatmospheric pressure chamber or the superatmospheric pressure chamber or the spring chamber.

It is necessary for the liquid to be injected in a patient to be free of air bubbles, and in order to attain this the liquid in the reservoir has to be free of air bubbles. According to the invention this is possible due to a float situated on top of the liquid in the reservoir, wherein an opening in the upper wall of the reservoir connects the part of the reservoir above the float with the atmosphere and wherein the float movably seals airtight against the side wall of the reservoir.

Preferably the invented device, after the reservoir having for instance a content of 10 cc has been emptied in 10 days by injecting for instance 5 doses of 0.2 cc a day, is thrown away and replaced by a new device, the reservoir of which has been filled and sealed in the factory. By sealing the reservoir it is avoided that a patient would fill the reservoir for repeated use of the device which would entail the danger of contaminations and/or air bubbles occurring in the liquid.

In order to be able to apply the device with a cannula which remains stuck in the patient in order to avoid infection, while the device itself is connected time and again to the cannula for injecting a dose of liquid, an embodiment of the invented device is characterized in that on the connecting element a cannula is removably mountable.

The invention is now elucidated by the following description of embodiments of the invented device, which have been indicated in the accompanying drawing.

FIG. 3 is a cross-section as according to FIG. 1, but in which the pump chamber has been completely emptied.

FIG. 4 is a cross-section as according to FIG. 1, but during filling, wherein the pump chamber has been drawn partially filled and the valve portion between the reservoir and the pump chamber is open.

Figures 1, 2:
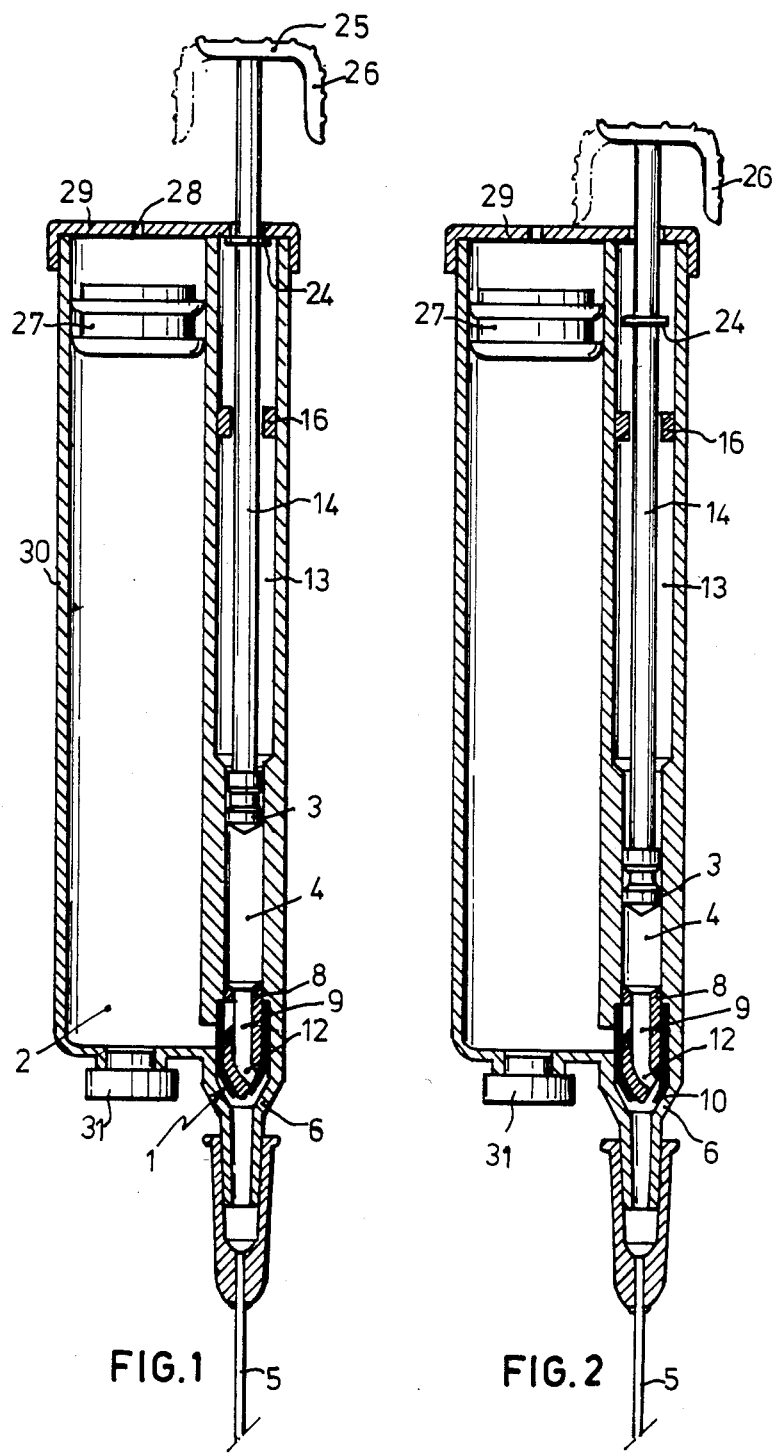
FIG. 1 is a longitudinal section through a first embodiment of the invented device, wherein the pump chamber is completely filled and wherein the subatmospheric pressure automatically draws the piston in the position in which the pump chamber is completely filled.
FIG. 2 is a cross-section as according to FIG. 1, but during emptying, wherein the pump chamber has been drawn partially emptied and the valve portion between the pump chamber and the cannula is open.

The drawn embodiments of the invented device are suitable for administering insulin, but the device can also be applied for administering other liquids such as for instance an antibiotic, or a carcinoma patient can administer a painkiller to himself as required by means of the invented device. The device can be used for subcutaneous, intravenous and/or intramuscular administering of liquid and it can be applied in an infusion set for parenteral administerings.

For instance for an ambulant diabetes patient it is necessary to keep a supply of insulin at home in order to administer several times a day an accurately measured out quantity of insulin, for example 0.2 cc, for example 2 or 3 times a day to himself. For that purpose the invented device according to FIG. 1 comprises a piston 4 being reciprocatably disposed in a pump chamber 4. The pump chamber is closed at the bottom end by a valve 1 consisting of a sleeve 10 about a body 8, wherein a channel 9 according to FIG. 2 extends through the body between the pump chamber 4 and a connecting element 6 to which a cannula 5 is connectable. Moreover a passage 7 according to FIG. 3 extends from channel 9 through the body 8 to the outlet 11 of a reservoir 2 for liquid to be administered.

The sleeve 10 of the valve 1 is of elastic, rubber-like material and in unburdened condition closes off both the outlet 12 of the channel 9 to the cannula 5 and the outlet 11 of the reservoir 2 to the passage 7. By according to FIG. 2 pushing down the piston liquid is pressed out of the pump chamber 4 and the sleeve 10 is pushed aside elastically from the outlet 12 so that liquid from the pump chamber 4 through passage 9 flows to the connecting element 6 and is injected via the cannula 5 into the patient. After the pump chamber 4 has been emptied and thus the piston cannot be pushed down any further, the pressure in channel 9 drops again to atmospheric pressure which causes the sleeve portion 10 near the outlet 12 to spring back elastically from the open position according to FIG. 2 to the closed position according to FIG. 3.

After the pump chamber 4 according to FIG. 3 has been emptied, the piston 3 according to FIG. 4 is moved upwards until the position according to FIG. 1 has been reached again. When moving the piston 3 upwards, subatmospheric pressure occurs in channel 9 in the valve 1, so that the outlet 12 of the channel 9 is kept closed by the sleeve 10, while near the passage 7 the sleeve 10 according to FIG. 4 turns to the right, which is possible since the upper rim of the sleeve reaches exactly up to the upper side of the passage 7. On account of this, liquid can flow from the reservoir 2 past the opened passage 7 via channel 9 to the pump chamber 4, so that at the highest position of the piston 3 according to FIG. 1 the pump chamber is completely filled. Then emptying the pump chamber 4 according to FIG. 2 up to situation according to FIG. 3 and refilling the pump chamber according to FIG. 4 in the above-described manner can take place. During emptying the pump chamber 4 due to superatmospheric pressure in the channel 9 and the passage 7 in the valve 1, the sleeve 10 is pushed against the outlet 11 of the reservoir 2 so that said outlet is then closed since the sleeve 10 completely seals said outlet 11 up to above said outlet, which is contrary to the passage 7, wherein the sleeve 10 reaches only up to the upper wall of the passage 7.

In this manner the invention provides a cheap and therefore disposable valve 1 comprising a body 8 of rigid plastic and an elastic sleeve 10 of elastic plastic. Nevertheless this cheap valve acts as a double check valve, that is under subatmospheric pressure (filling the pump chamber 4) the passage 7 according to FIG. 4 between the reservoir 2 and the pump chamber 4 is open while outlet 12 to the cannula 5 is closed, whereas under superatmospheric pressure (emptying the pump chamber 4) the outlet 11 of the reservoir 2 is closed while outlet 12 according to FIG. 2 between the pump chamber 4 and the cannula 5 is open.

The valve body 8 can be cylinder-shaped, wherein the outlet 12 of the channel 9 is radially directed, so that the connecting element 6 opposite the outlet 12 has to offer sufficient space for the sleeve 10 to diverge to the open position, for which purpose the connecting element 6 has to rather wide. A less voluminous connecting element 6 is possible because preferably the end of the valve body 8 facing away from the pump chamber is cone-shaped, wherein the outlet 12 of the channel 9 debouches at the cone surface and inclines with respect to the central axis of the valve body 8 as according to FIG. 2. From FIG. 2 it then appears that the diameter of the connecting element 6 about the cilinder-shaped portion of the valve body 8 is small because the outlet 12 is inclined downwardly in the cone-shaped portion of the valve body 8.

An important part of the invented device is an appliance which automatically provides each dose with the accurate desired quantity of liquid. For insulin this does is usually 0.2 cc, which is a slight quantity in which every deviation implies a high percentage of said slight quantity, whereas the invented device allows a deviation of 5 per cent, i.e. 0.1 cc, at the most. In known devices far larger deviations occur in the quantity of liquid due to careless use of the device. This careless use could arise from the fact that the patient trembles, has poor eyesight, has stiff joints, has failing mental abilities or suffers from other complaints due to old age, but also the device can be used carelessly because the patient is still a child.

These problems do not occur in the invented device since the piston 3 is automatically pushed from the position according to FIG. 3, in which the pump chamber has been completely emptied, to the position according to FIG. 1 in which the pump chamber 4 has been completely filled. In a first embodiment according to FIG. 1 through 4 of the invented device, automatically filling the pump chamber 4 is attained due to a subatmospheric pressure chamber 13 situated in alignment with the pump chamber 4 in which a pressure lower than subatmospheric pressure prevails, while the subatmospheric pressure chamber is sealed airtight with respect to the pump chamber by a partition 15 which is fixedly mounted on the piston rod 14 and which seals slidably against the wall portion above the pump chamber. The other end of the subatmospheric pressure chamber 13 is sealed airtight by a stationary partition 16 through which the piston rod extends slidably and in a sealing manner. Due to the subatmospheric pressure in the subatmospheric pressure chamber 13 and the atmospheric pressure prevailing in the reservoir 2 the liquid flows out of the reservoir according to FIG. 4 to the pump chamber 4 so that the piston automatically moves from its position according to FIG. 3 to the position according to FIG. 1 the moment the patient releases the push-button 25 of the piston 3. Because the device is disconnected with respect to the cannula 5, an atmospheric pressure prevails in the connecting element 6 due to which the sleeve 10 with its elastic abilities keeps the outlet 12 of the channel 9 closed. A cam 24 restricts the movement of the piston 3 by atmospheric pressure exerted by insulin in the pump chamber 4 and subatmospheric pressure above the piston 3 in the subatmospheric pressure chamber 13. Due to the above, the pump chamber 4 is filled every time with an equal quantity of liquid which moreover is completely free of air bubbles, so that the invented device is every time able to render equal doses of liquid without air bubbles, which is an important advantage of the invented device.

Figure 5:
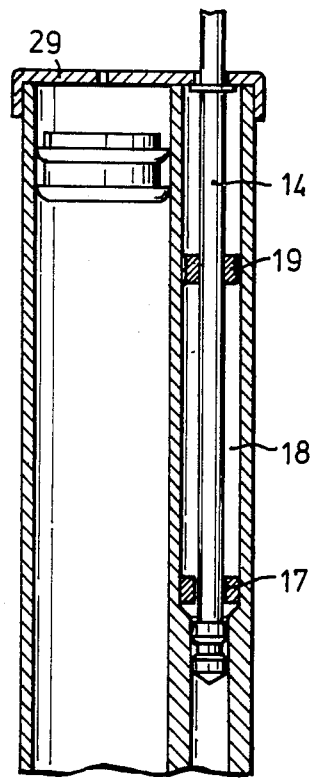
FIG. 5 is a-cross section as according to FIG. 1, but of a second embodiment of the invented device, in which superatmospheric pressure automatically draws the piston in the position in which the pump chamber is completely filled.

Instead of due to subatmospheric pressure, the piston 3 can also be automatically pushed out of the position according to FIG. 3 by superatmospheric pressure in an embodiment according to FIG. 5. This embodiment is equal to the above-described embodiment according to FIG. 1 through 4, with the exception of the fact that a superatmospheric pressure chamber 18 is situated in alignment with the pump chamber 4, said superatmospheric pressure chamber having a pressure higher than atmospheric pressure. The superatmospheric pressure chamber 18 is sealed airtight with respect to the pump chamber 4 by a stationary partition 17 through which the piston rod 14 extends slidably and in a sealing manner. The other end of the superatmospheric pressure chamber 18 is sealed airtight by a partition 19 which is fixedly mounted on the piston rod 14 and which seals slidably against the wall of the pressure chamber.

Figure 6:
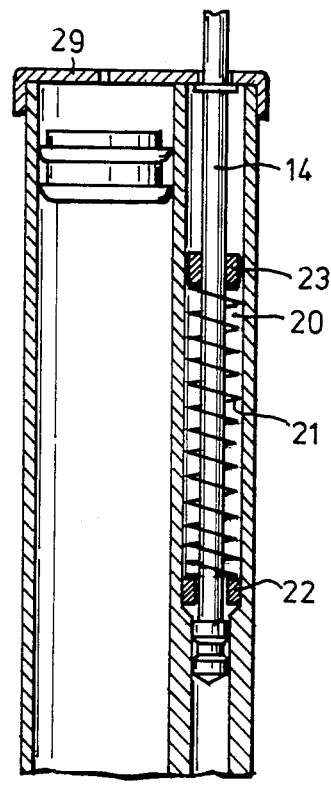
FIG. 6 is a cross-section as according to FIG. 1, but of a third embodiment of the invented device, provided with a helical spring to push the piston automatically into the position in which the pump chamber is completely filled.

In a third embodiment according to FIG. 6 of the invented device the piston can be automatically pushed, instead of by subatmospheric or superatmospheric pressure, by spring force out of the position according to FIG. 3 to the position according to FIG. 1. This embodiment according to FIG. 6 is equal to the above-described embodiments according to FIGS. 1 through 4 with the exception that a spring chamber 20 is situated in alignment with the pump chamber 4. In said spring chamber 20 is a spring 21 bearing on a support 22 secured near the pump chamber 4 and biasing against a cam 23 secured on the piston rod 14.

The pump chamber 4 can contain a normal dose of liquid to be injected, for instance 0.2 cc insulin, but often injection of a smaller dose, for instance with children, is necessary. Here too, injecting a very accurate smaller dose is of importance and therefore the invented device according to FIG. 1 has been provided with an operating button 25 having at least one appendix 26 extending downwardly along the piston rod 14 to such an extent as corresponds with the desired limited quantity of liquid to be administered from the pump chamber 4. The operating button 25 is mounted on the piston rod 14 onto which the piston 3 is mounted and for rendering a normal dose the operating button is pushed from the position according to FIG. 1 to the position according to FIG. 3, wherein the operating button 25 encounters the upper wall 29 of the device and wherein the appendix 26 according to FIG. 3 extends downwardly along the wall 32 of the device. For rendering a smaller dose than is possible with the content of the pump chamber 4, the operating button is first turned over 180°, so that the appendix 26 is turned into the position indicated by the dotted line in FIG. 1. If the operating button 25 is then pushed down, than the appendix 26 in the position indicated by the dotted line in FIG. 2 encounters the upper wall 29 of the device, so that the piston 3 can only empty a part of the pump chamber 4 and thus render a smaller, but accurate dose of the liquid, than would be possible if the piston could reach the position according to FIG. 3.

The invented device is extremely compact due to the fact that the reservoir 2 extends along the pump chamber 4 plus the subatmospheric pressure chamber 13 or the superatmospheric pressure chamber 18 or the spring chamber 20. It is necessary for the liquid to be injected into a patient to be free of air bubbles, which implies that the liquid in the reservoir 2 has to be free of air bubbles as well. According to the invention this is possible due to a float 27 situated on top of the liquid in the reservoir 2, wherein an opening 28 in the upper wall 29 of the reservoir connects the part of the reservoir above the float with the atmosphere and wherein the float movably seals airtight against the side wall 30 of the reservoir. Because of this, the liquid in the reservoir is always completely separated from the air above the float so air bubbles in the liquid are impossible.

Preferably the invented device is disposed of after the content, for example 10 cc insulin, of the reservoir has been used and the device is replaced by a new device, the reservoir 2 of which has been filled and sealed in the factory. By sealing the filling opening 31 of the reservoir 2 it is avoided that the patient fills the reservoir for repeated use of the invented device, which would cause danger for contamination and/or air bubbles occurring in the liquid. After the reservoir has been emptied, the device should be disposed of, and for that reason the invented device is manufactured of such a material and in such a way that the invented device is cheap and therefore edisposable. This can be attained by manufacturing the device mainly from plastic, but of course other materials can also be applied.

In order to avoid infection, the cannula is not stuck into the patient for each dose, since it could have been made insufficiently sterile by the patient, who is a layman in the field of medicine. Therefore it is customary to apply a so-called permanent cannula, which remains stuck into the patient for several days. The invented device can be adapted to this by forming the connecting element 6 in such a way that the connecting element can be mounted disconnectably on the permanent cannula 5.

The disadvantages of every time filling a hypodermic syringe from an ampul for every dose are also avoided if in the invented device the reservoir 2 and the rest of the device are two separate parts with respect to each other. Preferably, however, the reservoir and the rest of the device form an integral entity. If the reservoir is a separate part with respect to the device, then the reservoir and the rest of the device are provided with connecting elements which can be designed by an expert without any trouble and for that reason have not been explained further here.

I claim:

1. A device for administering a liquid in a number of doses, such as insulin to a patient, said device comprising a piston being reciprocatably disposed in a pump chamber, a cannula being connectible to the pump chamber and a piston rod connected to the piston and having an operating button characterized by a valve (1) and a reservoir (2) wherein by retracting the piston (3), at the same time the reservoir is connected to the pump chamber (4) through the valve in order to fill the pump chamber and the valve is moved into the position for closing the connecting element (6) between the pump chamber and the cannula (5) and wherein, by moving the piston forward, at the same time the connecting element between the pump chamber and the cannula is connected through the valve to the pump chamber and the valve is moved into the position for closing the passage (7) between the reservoir and the pump chamber, and the valve consists of a sleeve (10) about a body (8), a channel (9) extending through the body, between the pump chamber and the connecting element (6) for the cannula and the passage in the body branching off from the chanenl and communicating with the reservoir and in that the sleeve is of elastic material and in unburdened condition closes off both the outlet (12) of the channel to the cannula and the outlet (11) of the reservoir to the passage, whereas the sleeve portion of the outlet of the channel can only be pushed aside elastically by piston pressure exerted in the pump chamber and the upper rim of the sleeve reaches exactly up to the upper side of the passage of the reservoir, so that under subatmospheric pressure created by retracting the piston in the pump chamber, the sleeve contracts elastically so that the passage is open, whereas the sleeve near the passage completely covers the outlet of the reservoir during superatmospheric pressure in the passage.

2. A device according to claim 1, characterized in that the end of the valve body (8) facing away from the pump chamber (4) is coneshaped, wherein the outlet (12) of the channel (9) debouches at the cone surface and inclines with respect to the central axis of the valve body.

3. A device according to claim 1 or 2, characterized by a subatmospheric pressure chamber (13) which is situated in alignment with the pump chamber (4) and in which a pressure lower than atmospheric pressure prevails, wherein the subatmospheric pressure chamber is sealed airtight with respect to the pump chamber (4) by a partition (15) which is fixedly mounted on the piston rod (14) and which seals slidably against the wall portion above the pump chamber and wherein the other end of the subatmospheric pressure chamber is sealed airtight by a stationary partition (16) through which the piston rod extends slidably and in a sealing manner.

4. A device according to any claim 1 or 3, characterized by a superatmospheric pressure chamber (18) which is situated in alignment with the pump chamber (4) and in which a pressure higher than atmospheric pressure prevails, wherein the superatmospheric pressure chamber is sealed airtight with respect ot the pump chamber (4) by a stationary partition (17) through which the piston rod (14) extends slidably and in a sealing manner and wherein the other end of the superatmospheric pressure chamber is sealed airtight by a partition (19) which is mounted fixedly on the piston rod and which slidably seals against the wall of the superatmospheric pressure chamber.

5. A device according to claim 1 or 3, characterized by a spring chamber (20) which is situated in alignment with the pump chamber (4) and which contains a spring (21) bearing on a support (22) secured near the pump chamber (4) and biasing against a cam (23) secured on the piston rod (14).

6. A device according to claim 1 or 2, characterized in that the operating button (25) is provided with at least one appendix (26) extending downwardly along the piston rod (14) to such an extent as corresponds with the desired limited quantity of liquid to be administered from the pump chamber (4), wherein this appendix encounters the upper wall (29) of the device when pushing the piston (3), and wherein the piston, the piston rod (14) and the operating button are rotatable about their central axes in order to rotate the appendix into a position alongside the upper wall of the device in order to be able to empty the pump chamber completely.

7. A device according to claim 1, or 2, characterized in that the reservoir (2) extends along the pump chamber (4) plus the subatmospheric pressure chamber (13) or the superatmospheric pressure chamber (18) or the spring chamber (20).

8. A device according to claim 1, or 2, characterized by a float (27) situated on top of the liquid in the reservoir (2), wherein an opening (28) in the upper wall (29) of the reservoir connects the part of the reservoir above the float with the atmosphere and wherein the float movably seals airtight against the side wall (30) of the reservoir.

9. A device according to claim 9, characterized by a filling gate (31) for the reservoir near the valve (1).

10. A device according to claim 1, or 2, characterized in that on the connecting element (6) a cannula is removably mountable.

11. A device according to claim 1, or 2, characterized in that the device has been made of such a material and in such a manner that the device is disposable.

12. A device according to claim 1, or 2, characterized in that the reservoir (2) is removably mountable on the rest of the device.

13. A device for administering a liquid in a number of doses, such as insulin to a patient, said device comprising a piston being reciprocatably disposed in a pump chamber, a cannula being connectable to the pump chamber and a piston rod connected to the piston having an operating button, characterized by a valve (1) and a reservoir (2) wherein by retracting the piston (3), at the same time the reservoir is connected to the pump chamber (4) through the valve in order to fill the pump chamber and the valve is moved into the position for closing the connecting element (6) between the pump chamber and the cannula (5) and wherein, by moving the piston forward, at the same time the connecting element between the pump chamber and the cannula is connected through the valve to the pump chamber and the valve is moved into the position for closing the passage (7) between the reservoir and the pump chamber, a subatmospheric pressure chamber (13) is situated in alignment with the pump chamber and in which a lower than atmospheric pressure prevails, wherein the subatmospheric pressure chamber is sealed air tight with respect to the pump chamber by a partition (15) which is fixedly mounted on a piston rod (14) and which seals slideably against the wall portion above the pump chamber and wherein the other end of the subatmospheric pressure chamber is sealed air tight by a stationary partition (16) through which the piston rod extends slideably and in a sealing manner.

14. A device for administering a liquid in a number of doses such as insulin to a patient, said device comprising a piston being reciprocatably disposed in a pump chamber, a cannula being connectable to the pump chamber and a piston rod connected to the piston having an operating button, characterized by a valve (1) and a reservoir (2) wherein by retracting the piston (3), at the same time the reservoir is connected to the pump chamber (4) through the valve in order to fill the pump chamber and the valve is moved into the position for closing the connecting element (6) between the pump chamber and the cannula (5) and wherein, by moving the piston forward, at the same time the connecting element between the pump chamber and the cannula is connected through the valve to the pump chamber and the valve is moved into the position for closing the passage (7) between the reservoir and the pump chamber, and a superatmospheric pressure chamber (18) is situated in alignment with the pump chamber and in which a pressure higher than atmospheric pressure prevails, wherein the superatmospheric pressure chamber is sealed air tight with respect to the pump chamber by a statutory partition (17) through which the piston rod (14) extends slideably in a sealing manner and wherein the other end of the superatmospheric pressure chamber is sealed air tight by a partition (19) which is mounted fixedly on the piston rod and which slideably seals against the wall of the superatmospheric pressure chamber.

15. A device for administering a liquid in a number of doses, such as insulin to a patient, said device comprising a piston being reciprocatably disposed in a pump chamber, a cannula being connectable to the pump chamber and a piston rod connected to the piston and having an operating button, characterized by a valve (1) and a reservoir (2) wherein by retracting the piston (3), at the same time the reservoir is connected to the pump chamber (4) through the valve in order to fill the pump chamber and the valve is moved into the position for closing the connecting element (6) between the pump chamber and the cannula (5) and wherein, by moving the piston forward at the same time the connecting element between the pump chamber and the cannula is connected through the valve to the pump chamber and the valve is moved into the position for closing the passage (7) between the reservoir and the pump chamber, and the reservoir extends along the pump chamber and the subatmospheric pressure chamber, or the superatmospheric pressure chamber, or the spring chamber.

16. A device for administering a liquid in a number of doses, such as insulin to a patient, said device comprising a piston being reciprocatably disposed in a pump chamber, a cannula being connectable to the pump chamber and a piston rod connected to the piston and having an operating button, characterized by a valve (1) and a reservoir (2) wherein by retracting the piston (3) at the same time the reservoir is connected to the pump chamber (4) through the valve in order to fill the pump chamber and the valve is moved into the position for closing the connecting element (6) between the pump chamber and the cannula (5) and wherein by moving the piston forward, at the same time the connecting element between the pump chamber and the cannula is connected through the valve to the pump chamber and the valve is moved into the position for closing the passage (7) between the reservoir and the pump chamber, and a float (27) situated on top of the liquid in the reservoir, wherein an opening (28) in the upper wall (29) of the reservoir connects the part of the reservoir above the float with the atmosphere and wherein the float moveably seals air tight against the side wall (30) of the reservoir.

17. A device for administering a liquid in a number of doses as claimed in claim 16, further including a filling gate (31) for the reservoir near the valve.

* * * * *